US012723017B2

(12) United States Patent
Palomino

(10) Patent No.: US 12,723,017 B2
(45) Date of Patent: Sep. 1, 2026

(54) 2,5,6-TRICHLORODOPAMINE: SYNTHESIS AND APPLICATIONS

(71) Applicant: WALKER CANCER RESEARCH INSTITUTE, INC., Boynton Beach, FL (US)

(72) Inventor: Eduardo Palomino, Troy, MI (US)

(73) Assignee: Walker Cancer Research Institute, Inc., Boynton Beach, FL (US)

( * ) Notice: Subject to any disclaimer, the term of this patent is extended or adjusted under 35 U.S.C. 154(b) by 454 days.

(21) Appl. No.: 18/390,489

(22) Filed: Dec. 20, 2023

(65) Prior Publication Data

US 2025/0206695 A1 Jun. 26, 2025

(51) Int. Cl.
*C07C 215/52* (2006.01)
*C07C 213/08* (2006.01)
*C07C 213/10* (2006.01)
*C07C 215/46* (2006.01)

(52) U.S. Cl.
CPC .......... *C07C 215/46* (2013.01); *C07C 213/08* (2013.01); *C07C 213/10* (2013.01)

(58) Field of Classification Search
None
See application file for complete search history.

(56) References Cited

U.S. PATENT DOCUMENTS

| | | | |
|---|---|---|---|
| 6,692,632 | B1 | 2/2004 | Bremner et al. |
| 8,313,619 | B2 | 11/2012 | Joshi et al. |
| 8,696,997 | B2 | 4/2014 | Hancok |
| 2019/0076507 | A1 | 3/2019 | Sakai et al. |
| 2022/0204354 | A1 | 6/2022 | Palomino |
| 2022/0306597 | A1 | 9/2022 | Palomino |
| 2023/0102045 | A1 | 3/2023 | Palomino |

FOREIGN PATENT DOCUMENTS

WO 2017/150637 A1 9/2017

OTHER PUBLICATIONS

Jeitner et al. Inflaming the diseased brain: a role for tainted melanins, Biochimica et Biophysica (BBA)—Molecular Basis of Disease, Acta, 2015, vol. 1852, Issue 5, pp. 937-950—Published Jan. 10, 2015; ISSN 0925-4439 (Year: 2015).*

(Continued)

*Primary Examiner* — Kortney L. Klinkel
*Assistant Examiner* — Pauline Ondachi
(74) *Attorney, Agent, or Firm* — Brooks Kushman P.C.

(57) ABSTRACT

A compound having formula 1 or a salt thereof:

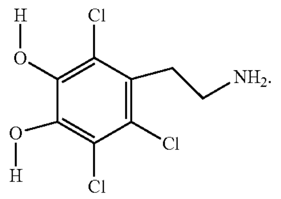

1

A method for making the compound having formula 1 includes a step of reacting dopamine·HCl with hypochlorous acid in a reaction solvent to form the compound having formula 1 or a salt thereof. The reaction can take place in a polar or nonpolar solvent.

19 Claims, 3 Drawing Sheets

(56) References Cited

OTHER PUBLICATIONS

Anelli, P.L. et al., "Oxidation of Diols with Alkali Hypochlorites Catalyzed by Oxammonium Salts Under Two-Phase Conditions," J. of Organic Chemistry (1989), 54(12), pp. 2970-2972.
Bisaglia, M. et al., "Kinetic and Structural Analysis of the Early Oxidation Products of Dopamine," J. Biol. Chem v. 282, n. 21, (2007), pp. 15597-155605.
Block, M.S. et al., "Hypochlorous Acid: A Review," J. Oral Maxillofacial Surg 78 (2020), pp. 1461-1466.
Brown, K.C. et al., "Benzoquinone Imines. Part 16. Oxidation of p-Aminophenol in Aqueous Solution," J. Chem. Soc., Perkin Trans. 2, 1979, pp. 308-311.
Castagna, R. et al., "Hydroxyl Radical From the Reaction Between Hypochlorite and Hydrogen Peroxide," Atmospheric Environment, (2008), v. 42, pp. 6551-6554.
Cort, W.M. et al., "Antioxidant Activity and Stability of 6-Hydroxy-2,5,7,8-Tetramethylchroman-2-Carboxylic Acid," J. Am. Oil Chem. Soc., 52(6) (1975), pp. 174-178.
Darwich, C. et al., "Chlorine-Atom Transfer Reactions between Chloramine (=Chloramide) and Piperidine: Kinetic Reactivitya nd Characterization in a Raschig Medium," Helvetica Chimica Act, v. 92 (2009), pp. 98-111.
Dorwald, F.Z., "Side Reactions in Organic Synthesis," Wiley-VCH 2005, 37 pgs.
Dowd, P. et al., "On the Mechanism of the Anticlotting Action of Vitamin E Quinone," Proc. Natl. Acad. Scie. USA, v. 92, 1995, pp. 8171-8175.
Fuhlhage, D.W. et al., "Studies on the Formation and Reactions of 1-Pyrroline," J. of the American Chem Society, 1958, 80, pp. 6249-6254.
Greaves, J. et al., "Sodium hypochlorite disinfection of SARS-CoV-2 spiked in water and municipal wastewater," Science of the Total Environment 807 (2022), 150766, 5 pgs.
Ho, H. et al., "Oxidation of 2,2,7,8-tetramethyl-6-chromanol, the model compound of γ-tocopherol, by hypochlorous acid," Redox Report, v. 5. n. 1 (2000), 4 pgs.
Hashemi, M. et al., "Sodium Hypochlorite/Dowex 1X8-200: an Effective Oxidant for the Oxidation of Aromatic Amines to Quinones," J. Chem. Research, (S) (1999), 11, pp. 672-673.
Holleman, A.F., "4.3.1. Hypochlorous Acid, HCIO," Inorganic Chemistry 2001, pp. 442-444.
Ishihara, M. et al., "Stability of Weakly Acidic Hypoghlorous Acid Solution with Microbicidal Activity," Biocontrol Science, 2017, v. 22, n. 4, pp. 223-227.
Ito, et al., Ferric Salt Catalyzed Oxygenation of Cycloalkanones to Oxo Esters by Molecular Oxygen, J. Org. Chem., 48, (1983), pp. 1133-1135.
Jeitner, T.M. et al., "Linking Inflammation and Parkinson Disease: Hypochlorous Acid Generates Parkinsonian Poisons," Toxicological Sciences, 151(2), 2016, pp. 388-402.
Khan, A.A. et al., "Myeloperoxidase as an Active Disease Biomarker: Recent Biochemical and Pathological Perspectives," Qassin University, Medical Sciences, 2018, 6, 33, 21 pgs.
Larisch et al., "Reactions of Dehydroascorbic Acid with Primary Aliphatic Amines Including N-Acetyllysine)," J. Agric. Food Chem. 1996, 44, pp. 1630-1634.
Lerner, L., "Identity of a Purple Dye Formed by Peroxidic Oxidation of p-Aminophenol at Low pH," J. Phys. Chem. A 2011, 115, pp. 9901-9910.
Lyu, Q. et al., "Unravelling the polydopamine mystery: is the end in sight?" Polymer Chemistry, 2019, 10, pp. 5771-5777.
Monaco, M.R. et al., "Biomimetic Organocatalytic Asymmetric Synthesis of 2-Substituted Piperidine-Type Alkaloids and their Analogues," Organic Letters (2011), 13(17), pp. 4546-4549.
"OxyChem Sodium Hypochlorite Handbook." Sodium Hypochlorite Handbook <Dec. 2014), 25 pgs.
Paris, I. et al., "Aminochrome Induces Disruption of Actin, Alpha-, and Beta-Tuulin Cytoskeleton Networks in Substantia-Nigra-Derived Cell Line," Neurotox Res. (2010) 18, pp. 82-92.
Sakurai, H. et al., "Structure and Ninhydrin Reaction Mechanism of the Ninhydrin-positive Substance Produced by the Reaction of Dehydroascorbic Acid wih Glycyl Dipeptides," Boll. Coll. Agr. & Vet Med., Nihon Univ., No. 45, (1988), pp. 59-70 (English Abstract—rest of article is in Japanese).
Singh, Y.P. et al., "Studies on the Complexes of Some Basic Dyes With Hexacyanoferrates," J. of Indian Chem Soc., 19179, 56(6), 1979, 559-61.
Thomas, M.J. et al., "Oxidation and Reaction of Trolox c, a Togopheral Analogue, in Aqueous Solution. A Pulse-Radiolysis Study," J. Am. Chem. Soc. (1989), v. 111, n. 9, pp. 3315-3319.
Yang, C.S. et al., "Does Vitamin E Prevent or Promote Cancer?," Cancer Prev. Res. (Phila), 2012, 5(5), pp. 701-705.
Non-final Office Action dtd Jan. 30, 2024 for U.S. Appl. No. 17/394,680, filed Aug. 5, 2021, 14 pgs.
Non-Final Office Action dtd Feb. 24, 2023 for U.S. Appl. No. 17/394,680, filed Aug. 5, 2021, 17 pgs.
Final Office Action dtd Jul. 21, 2023 for U.S. Appl. No. 17/394,680, filed Aug. 5, 2021, 16 pgs.
Non-Final Office Action dtd Nov. 22, 2021 for U.S. Appl. No. 17/212,186, filed Mar. 25, 2021, 7 pgs.
Final Office Action dtd Mar. 14, 2022 for U.S. Appl. No. 17/212,186, filed Mar. 25, 2021, 5 pgs.
Advisory Action dtd May 27, 2022 for U.S. Appl. No. 17/212,186, filed Mar. 25, 2021, 3 pgs.
Non-Final Office Action dtd Jan. 18, 2022 for U.S. Appl. No. 17/139,347, filed Dec. 31, 2020, 6 pgs.
Final Office Action dtd Apr. 15, 2022 for U.S. Appl. No. 17/139,347, filed Dec. 31, 2020, 8 pgs.
Non-Final Office Action dtd Jul. 1, 2022 for U.S. Appl. No. 17/139,347, filed Dec. 31, 2020, 6 pgs.
Final Office Action dtd Aug. 23, 2022 for U.S. Appl. No. 17/139,347, filed Dec. 31, 2020, 6 pgs.
Advisory Action dtd Oct. 31, 2022 for U.S. Appl. No. 17/139,347, filed Dec. 31, 2020, 3 pgs.
Examiner's Answer dtd Apr. 4, 2023 for U.S. Appl. No. 17/139,347, filed Dec. 31, 2020, 7 pgs.
STN Database, CAS registry No. 118665-35-3, submitted Jan. 27, 1989.
Lister, M.W., "The Decomposition of Hypoghlorous Acid," Canadian J. of Chemistry, 1952, 30, pp. 879-889.
Zhou, Z. et al., "Oxidation of Celulose and Carboxylic Acids by Hyochlorous Acid: Kinetics and Mechanisms," J. of Pulp and Paper Science, v. 34, n. 4, 2008, pp. 1-7.
Final Office Action dated May 23, 2024 for U.S. Appl. No. 17/394,680, filed Aug. 5, 2021, 15 pgs.

* cited by examiner

Mechanism of Reaction of Dopamine (DP) with Hypochlorous Acid (HClO)

NET:

2DP + 3HClO → DPCR + DPCl3 + 3H2O

2,5,6-TRICHLORODOPAMINE: SYNTHESIS AND APPLICATIONS

TECHNICAL FIELD

In at least one aspect, the present invention is related to methods and compositions for producing 2,5,6-trichlorodopamine.

BACKGROUND

Catecholamines are monoamine neurotransmitters that are organic compounds having a catechol (i.e., benzene with two adjacent hydroxyl groups) and a side-chain amine. Examples of catecholamines include dopamine (i.e., 3,4-dihydroxyphenethylamine) and adrenaline (i.e., (R)-4-(1-hydroxy-2-(methylamino)ethyl)benzene-1,2-diol.) Dopamine is a neuromodulator molecule classified that plays several important roles in humans. It constitutes about 80% of the catecholamine content in the brain and is synthesized from L-DOPA made in the brain and kidneys of humans. Dopamine is also synthesized in plants and most animals where it functions as a neurotransmitter. (Goodman and Gilman's: The pharmacological basis of therapeutics, 8th Ed, p. 200-201)

Recently, dopamine has attracted interest in chemistry and biomedical research owing to its adhesive potential for wound closure. Under alkaline conditions, the catechol functional group of dopamine oxidizes to quinone with self-polymerizing capabilities and thin film formation via strong intermolecular forces like hydrogen bonding, metal chelation, and π-π interaction (Mussel-inspired hydrogel tissue adhesives for wound closure. (M. Rahimnejad and W Zhong RSC Adv., 2017, 7, 47380).

Accordingly, there is a need for improved methods for making catecholamines such as dopamine and derivatives thereof.

SUMMARY

In at least one aspect, a method for preparing a compound having formula 1 and/or a salt thereof is provided:

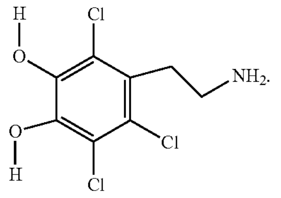

1

The method includes a step of reacting dopamine·HCl with hypochlorous acid in a reaction solvent to form the compound having formula 1 or a salt thereof.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

For a further understanding of the nature, objects, and advantages of the present disclosure, reference should be had to the following detailed description, read in conjunction with the following drawings, wherein like reference numerals denote like elements and wherein.

DETAILED DESCRIPTION

Figure 1:
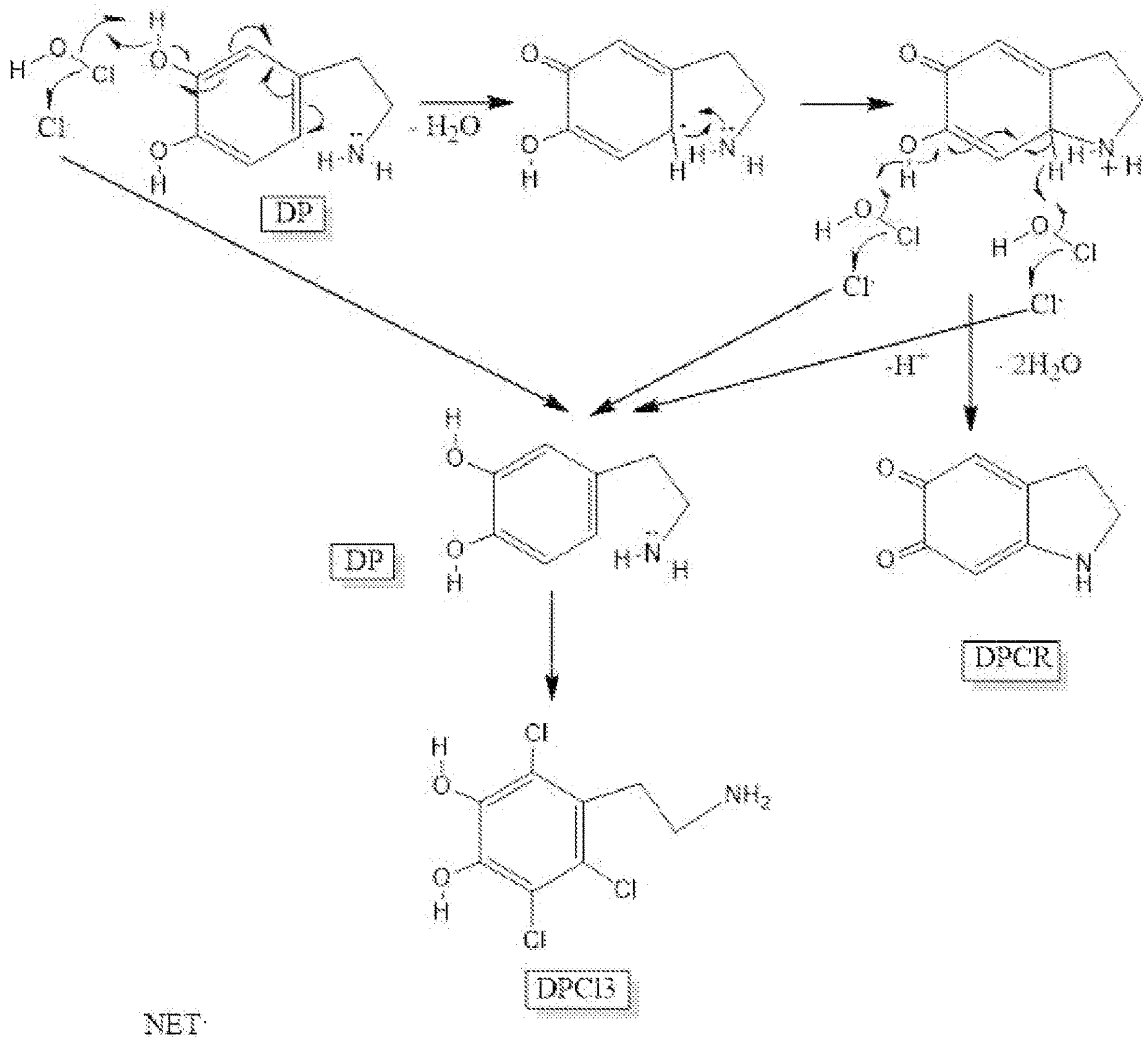
FIG. 1. Mechanism scheme for making 2,5,6-trichlorodopamine by the reaction of dopamine with pure hypochlorous acid.

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

With respect to the terms "comprising," "consisting of," and "consisting essentially of," where one of these three terms is used herein, the presently disclosed and claimed subject matter can include the use of either of the other two terms.

The phrase "composed of" means "including" or "comprising." Typically, this phrase is used to denote that an object is formed from a material.

It should also be appreciated that integer ranges explicitly include all intervening integers. For example, the integer range 1-10 explicitly includes 1, 2, 3, 4, 5, 6, 7, 8, 9, and 10. Similarly, the range 1 to 100 includes 1, 2, 3, 4 . . . 97, 98, 99, 100. Similarly, when any range is called for, intervening numbers that are increments of the difference between the upper limit and the lower limit divided by 10 can be taken as alternative upper or lower limits. For example, if the range is 1.1. to 2.1 the following numbers 1.2, 1.3, 1.4, 1.5, 1.6, 1.7, 1.8, 1.9, and 2.0 can be selected as lower or upper limits. In the specific examples set forth herein, concentrations, temperature, and reaction conditions (e.g., pressure, pH, etc.) can be practiced with plus or minus 50 percent of the values indicated rounded to three significant figures. In a refinement, concentrations, temperature, and reaction conditions (e.g., pressure, pH, etc.) can be practiced with plus or minus 30 percent of the values indicated rounded to three significant figures of the value provided in the examples. In another refinement, concentrations, temperature, and reaction conditions (e.g., pH, etc.) can be practiced with plus or minus 10 percent of the values indicated rounded to three significant figures of the value provided in the examples.

In the examples set forth herein, concentrations, temperature, and reaction conditions (e.g., pressure, pH, flow rates, etc.) can be practiced with plus or minus 50 percent of the values indicated rounded to or truncated to two significant figures of the value provided in the examples. In a refinement, concentrations, temperature, and reaction conditions (e.g., pressure, pH, flow rates, etc.) can be practiced with plus or minus 30 percent of the values indicated rounded to or truncated to two significant figures of the value provided in the examples. In another refinement, concentrations, temperature, and reaction conditions (e.g., pressure, pH, flow rates, etc.) can be practiced with plus or minus 10 percent of the values indicated rounded to or truncated to two significant figures of the value provided in the examples.

Throughout this application, where publications are referenced, the disclosures of these publications in their entirety are hereby incorporated by reference into this application to more fully describe the state of the art to which this invention pertains.

The term "weak acid" refers to an acid having a $pK_a$ from 2 to 7.5.

The term "weak organic acid" refers to a carboxylic acid, dicarboxylic acid, or tricarboxylic acid having a $pK_a$ from 2 to 7.5. In a refinement, refers to a carboxylic acid, dicarboxylic acid, or tricarboxylic acid having a $pK_a$ of at least 2, 2.5, 3, 3.5, or 4 and of at most 7.5, 7, 6.5, 6, 5.5 or 5. Examples of weak organic acids include but are not limited to, acetic acid, formic acid, propionic acid, butyric acid, benzoic acid, lactic acid, and oxalic acid. It is noteworthy that acetic acid has a $pK_a$ of about 4.76.

The term "pure hypochlorous acid" means that the hypochlorous acid prepared from the methods below includes compounds other than hypochlorous acid in an amount of less than 1 weight percent. With respect to solutions, a pure hypochlorous acid solution includes compounds other than hypochlorous acid and the solvents in an amount of less than 1 weight percent.

In an embodiment, a compound having formula 1 (i.e., 2,5,6-trichlorodopamine) or a salt thereof is provided:

1

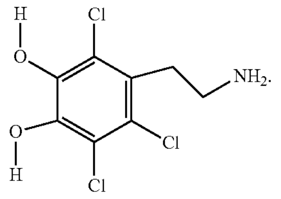

In a variation, as shown below in more detail, this compound is prepared by the reaction of dopamine hydrochloride and hypochlorous acid. In a refinement, the salt is a hydrochloride salt in which HCl reacts with the $NH_2$ group in formula 1. As set forth below, the compound having formula 1 or a salt thereof is prepared by the reaction of dopamine hydrochloride and hypochlorous acid.

Figure 2A:
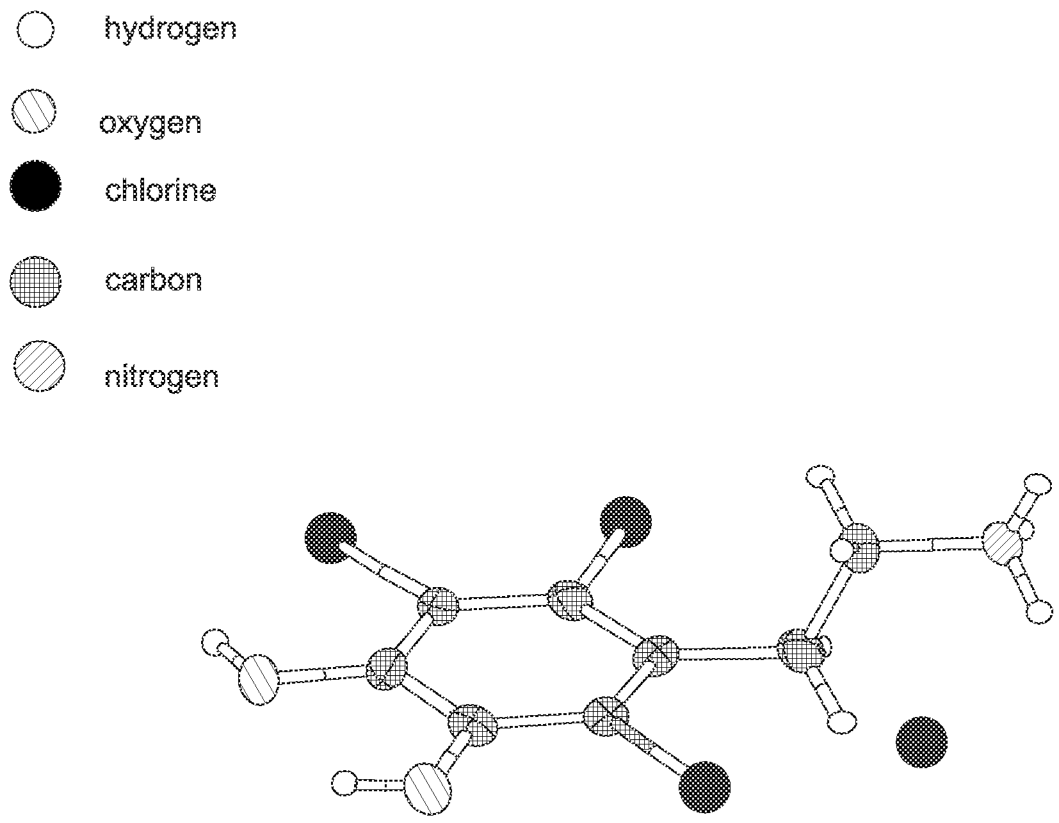
FIG. 2A. Crystal structure for 2,5,6-trichlorodopamine.
Figure 2B:
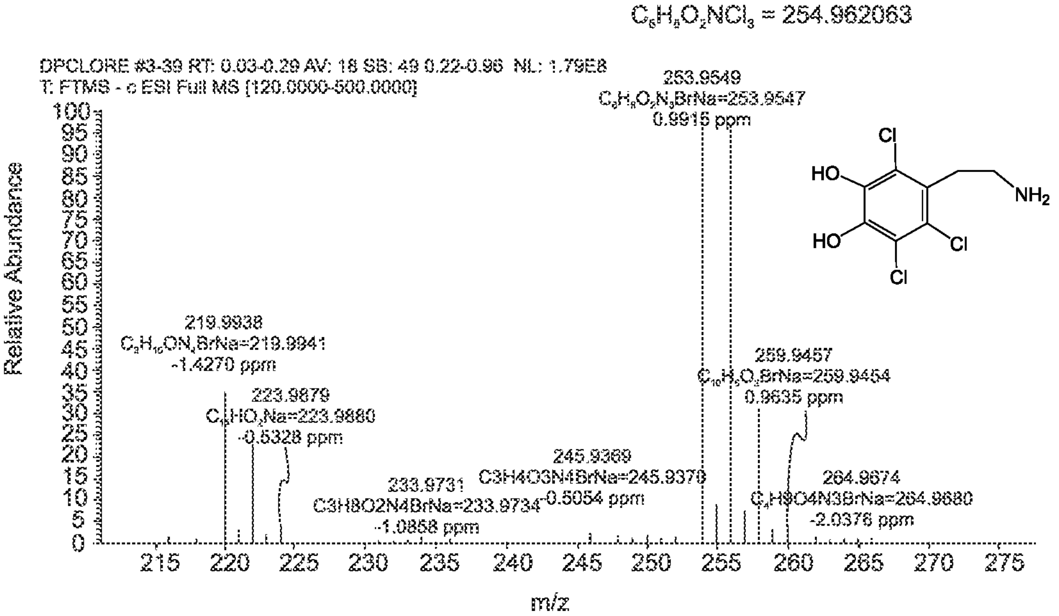
FIG. 2B. Mass spectrum for 2,5,6-trichlorodopamine.

In an embodiment, the preparation of a new derivative of dopamine in which three chlorine atoms replace the three hydrogens of the aromatic ring of the parent molecule dopamine is provided. The synthesis of 2,5,6-trichlorodopamine is made in one step by the action of pure hypochlorous acid on solid or aqueous dopamine hydrochloride. The only by-product of the reaction is dopaminochrome, another useful compound described in the literature as produced in the human body. The reaction follows the mechanism presented in FIG. 1. FIG. 2 shows the crystal structure and the mass spectroscopy of 2,5,6-trichlorodopamine.

In another aspect, the method is a one-step synthetic scheme for making 2,5,6-trichlorodopamine by the reaction of dopamine with pure hypochlorous acid, whose production method was recently discovered and described in US Pat. Appl. No < >; the entire disclosure of which is hereby incorporated by reference.

In another aspect, a method for preparing a compound having formula 1 and/or a salt thereof is provided:

1

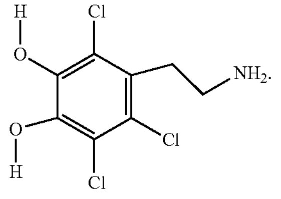

The method includes a step of reacting dopamine·HCl with hypochlorous acid in a reaction solvent to form the compound having formula 1 or a salt thereof. In a refinement, the molar ratio of hypochlorous acid to the dopamine·HCl is about 3:1. In some refinements, the molar ratio of hypochlorous acid to the dopamine·HCl is at least 2.7:1, 2.8:1, 2.9:1, 3:1, 3.3:1, or 3.4:1. In other refinements, the molar ratio of hypochlorous acid to the dopamine·HCl is at most 5:1, 4.5:1, 4:1, 3.8:1, 3.6:1, or 3.5:1. In a refinement, the reaction is carried out at a temperature from 30 to 30° C. (i.e., room temperature).

In another aspect, the reaction solvent is a polar solvent (e.g., water).

In another aspect, the reaction solvent is a nonpolar reaction solvent. In a refinement, the nonpolar reaction has a dielectric constant less than about 10. In a refinement, the nonpolar reaction is an aprotic solvent. An example of a useful nonpolar reaction solvent is ethyl acetate.

In another aspect, the hypochlorous acid used in the preparation of the compound having formula 1 is prepared by mixing aqueous sodium hypochlorite with a weak acid in a nonpolar solvent to form a biphasic mixture including an organic phase and an aqueous phase. In a refinement, the biphasic mixture is agitated. The aqueous phase is then discarded. In a further refinement, the organic phase is passed through silica gel. The nonpolar solvent is subsequently removed under vacuum to produce pure HOCl. In a refinement, the nonpolar solvent has a dielectric constant less than about 10. In a refinement, the nonpolar solvent is an aprotic solvent. An example of a useful nonpolar reaction solvent is ethyl acetate. In a refinement, the molar ratio of sodium hypochlorite to the weak acid is about 1:1. In some refinements, the molar ratio of sodium hypochlorite to the weak acid is at least 0.7:1, 0.8:1, 0.9:1, 1:1, 1.1:1, or 1.2:1. In other refinements, the molar ratio of sodium hypochlorite to the weak acid is at most 2:1, 1.5:1, 1.4:1, 1.3:1, 1.2:1, or 1.1:1.

In another aspect, the compound having formula 1 is used as a dopamine biomimetic for comparative studies with its precursor dopamine.

In another embodiment, a method for wound closure is provided. The method includes a step of identifying a subject having a wound in need of closure. Typically, such identification can be by visual inspection that shows a wound. A composition that includes a compound having formula 1 or a salt thereof is applied to the wound:

1

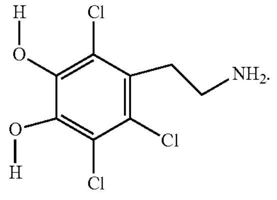

The following examples illustrate the various embodiments of the present invention. Those skilled in the art will recognize many variations that are within the spirit of the present invention and scope of the claims.

1. Synthesis of 2,5,6-trichlorodopamine 1.1 Method A: From Dopamine·HCl in Water A solution of 3.52 g of dopamine hydrochloride in 5 ml of water was mixed with 1.54 g of pure hypochlorous acid in a 100 ml beaker. The pure hypochlorous acid is prepared by mixing 50 ml of aqueous sodium hypochlorite 6% (bleach) with 2.4 g of pure acetic acid in 350 ml of ethyl acetate, shaking the biphasic mixture, decanting, and discarding the aqueous phase, passing the organic phase containing the HOCl through a plug of silica gel and removing the ethyl acetate under vacuum to produce pure HOCl as a clear, thick liquid. The solution from the mixing of dopamine hydrochloride with pure hypochlorous acid turned red-black upon standing. White crystals of 2,5,6-trichlorodopamine precipitated from the solution. The crystals were filtered and weighed to give 2.8 g of pure material (about 100% yield). The crystals were analyzed by x-ray diffraction and mass spectroscopy to produce the structure and diagram shown in FIG. 2. The red-black solution was concentrated under vacuum, and its NMR and mass spectroscopy analysis confirmed its structure as dopaminochrome.

1.2 Method B: From Solid Dopamine·HCl in Ethyl Acetate

To a solution of HOCl in 350 ml of ethyl acetate [prepared by mixing 50 ml of aqueous sodium hypochlorite 6% (bleach) with 2.4 g of pure acetic acid in 350 ml of ethyl acetate, shaking the biphasic mixture, decanting and discarding the aqueous phase, and passing the organic phase containing the HOCl through a plug of silica gel] in a 500 ml separatory funnel, were added 3.52 g of solid dopamine·HCl. The funnel was shaken intensely, with intervals for venting, for 20 minutes until all the dopamine·HCl had been converted from a white solid to a red-black syrup that separated at the bottom of the funnel from where it was separated. The organic phase (ethyl acetate) was decanted from the funnel and allowed to evaporate in a beaker to produce crystalline 2,5,6-trichlorodopamine that weighed 2.75 g and was deemed pure by 1H-NMR.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A compound having formula 1 or a salt thereof:

(1)

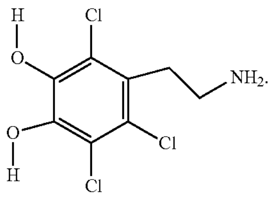

2. The compound of claim 1 prepared by the reaction of dopamine hydrochloride and hypochlorous acid.

3. The compound of claim 1 wherein the salt is a hydrochloride salt.

4. A method for preparing a compound having formula 1 and/or a salt thereof:

1

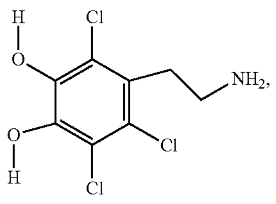

the method comprising:

reacting dopamine·HCl with hypochlorous acid in a reaction solvent to form the compound having formula 1 or a salt thereof.

5. The method of claim 4, wherein the reaction solvent is a polar solvent.

6. The method of claim 4, wherein the reaction solvent is water.

7. The method of claim 5, wherein hypochlorous acid is prepared by mixing aqueous sodium hypochlorite with a weak acid in a nonpolar solvent to form a biphasic mixture including an organic phase and an aqueous phase.

8. The method of claim 7, wherein the weak acid is acetic acid.

9. The method of claim 7, wherein the nonpolar solvent is ethyl acetate.

10. The method of claim 7, wherein the biphasic mixture is agitated.

11. The method of claim 10, wherein the aqueous phase is discarded.

12. The method of claim 11, wherein the organic phase is passed through silica gel.

13. The method of claim 12, wherein the nonpolar solvent is removed under vacuum to produce pure HOCl.

14. The method of claim 4, wherein the reaction solvent is a nonpolar solvent.

15. The method of claim 14, wherein the reaction solvent has a dielectric constant less than about 10.

16. The method of claim 14, wherein the reaction solvent is ethyl acetate.

17. The method of claim 4, wherein the molar ratio of hypochlorous acid to dopamine·HCl is about 3:1.

18. A method for wound closure comprising:

identifying a subject having a wound in need of closure; and applying a composition that includes a compound having formula 1 or a salt thereof to the wound:

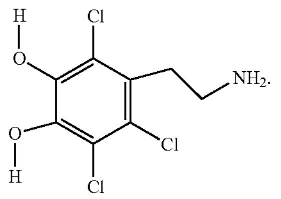

(1)

19. The method of claim 18, wherein the salt is a hydrochloride salt.

* * * * *